US008703414B2

(12) United States Patent
Tetzner

(10) Patent No.: US 8,703,414 B2
(45) Date of Patent: Apr. 22, 2014

(54) METHOD FOR THE QUANTIFICATION OF METHYLATED DNA

(75) Inventor: Reimo Tetzner, Berlin (DE)

(73) Assignee: Epigenomics AG, Berlin (DE)

( * ) Notice: Subject to any disclaimer, the term of this patent is extended or adjusted under 35 U.S.C. 154(b) by 990 days.

(21) Appl. No.: 11/989,190

(22) PCT Filed: Jul. 20, 2006

(86) PCT No.: PCT/EP2006/007288
§ 371 (c)(1),
(2), (4) Date: Jan. 22, 2008

(87) PCT Pub. No.: WO2007/009822
PCT Pub. Date: Jan. 25, 2007

(65) Prior Publication Data
US 2011/0104663 A1    May 5, 2011

(30) Foreign Application Priority Data

Jul. 21, 2005  (EP) .................................. 05090216

(51) Int. Cl.
*C12Q 1/68*    (2006.01)
(52) U.S. Cl.
USPC .......................................... 435/6.1; 435/91.2
(58) Field of Classification Search
None
See application file for complete search history.

(56) References Cited

U.S. PATENT DOCUMENTS

| | | | |
|---|---|---|---|
| 6,124,120 A | 9/2000 | Lizardi | |
| 6,331,393 B1 * | 12/2001 | Laird et al. | 435/6.12 |
| 8,137,616 B2 * | 3/2012 | Sagner et al. | 422/50 |
| 2010/0143893 A1 * | 6/2010 | Berlin | 435/6 |

FOREIGN PATENT DOCUMENTS

| | | |
|---|---|---|
| DE | 10029915 | 1/2002 |
| DE | 10154317 | 5/2003 |
| EP | 20040090213 | 5/2004 |
| WO | WO 00/70090 | 11/2000 |
| WO | WO00/70090 | * 11/2000 |
| WO | WO 02072880 | 9/2002 |
| WO | WO 03081532 | 10/2003 |
| WO | WO 2005038051 | 4/2005 |
| WO | WO 2005098035 | 10/2005 |

OTHER PUBLICATIONS

Cottrell et al. (Nucleic Acids Research, 2004, vol. 32, No. 1, e10, p. 1-8, edat Jan. 15, 2004).*
Rand et al. (Methods, 2002, p. 114-120).*
Lo et al. (Cancer Research, 1999, vol. 59, p. 3899-3903).*
Zeschnigk et al. (Nucleic Acids Research, 2004, 32(16):e125, p. 1-5).*
Heid et al. (Genome Res., 1996, 986-994).*
Gruber et al. Appl. Environ. Microbiol., 2001, 67(6):2837-2839.*
Bransteitter: "Activation-induced cytidine deaminase deaminates deoxycytidine on single-stranded DNA but requires the action of RNase" Proc, Natl. Acad. Sci. vol. 100, No. 7, 2003, pp. 4102-4107.
Eads et al: "Epigenetic Patterns in the Progression of Esophageal Adenocarcinoma" Cancer Research, vol. 61, 2001, pp. 3410-3418.
Fraga: "DNA methylation: a profile of methods and applications" Biotechniques, vol. 33, No. 3, 2002, p. 632.
Frommer: "A genomic sequencing protocol that yields a positive display of 5-methylcytosine residues in individual DNA strands" Proc. Natl. Acad.. Sci., vol. 89, No. 5, 1992, pp. 1827-1831.
Hawkins: Whole genome amplification—applications and advances' Curr. Opin. Biotechnol. vol. 13, No. 1, 2002, pp. 65-67.
Herman, et al: "Methylation-specific PCR: a novel PCR assay for methylation status of CpG islands". Proc. Natl. Acad. Sci., vol. 93, No. 18, 1996, pp. 9821-9826.
Kains: "The PCR plateau phase—towards an understanding of its limitations" Biochem. Biophy. Acta, vol. 1494, 2000, pp. 23-27.
Lehmann and Kreipe: "Real-time PCR-based assay for quantitative determination of methylation status" Methods Mai. Biol., vol. 287, 2004, pp. 207-218.
Lehmann: Quantitative assessment of promoter hypermethylation during breast cancer development' Am. J. Pathol., vol. 160, No. 2, 2002, pp. 605-612.
Livak. K, J.: "Allelic discrimination using fluorogenic probes and the 5' nuclease assay" Genetic Analysis: Biomolecular Engineering, vol. 14, 1999,-pp. 143-149.
Lo: "Allelic variation in gene expression is common in the human genome" Genome Res., vol. 13, No. 8, 2003, pp. 1855-1862.
Miller: "Five not four: History and significance of the fifth base" in The EPI-Genome' Wiley-VCH Verlag, 2003, pp. 3-20.
Nelson: "Detection of all single-base mismatches in solution by chemiluminescence" Nucleic Acids Res., vol. 24, No. 24, 1996, pp. 4998-5003.
Numerical recipes, 2002, Cambridge University Press.
Olek: "A modified and improved method for bisulphite based cytosine methylation analysis" Nucleic Acids Res. vol. 24, No. 24. 1996, pp. 5064-5066.
Oliver, D. H. et al.: "Use of single nucleotide polymorphisms (SNP) and real-time polymerase chain reaction for hone marrow engraftment analysis." The Journal of Molecular Diagnostics: vol. 2, No. 4, Nov. 2000, pp. 202-208.

(Continued)

*Primary Examiner* — Stephanie K Mummert
(74) *Attorney, Agent, or Firm* — DLA Piper LLP (US)

(57) ABSTRACT

The method according to the invention concerns in particular a method for the quantification of methylated DNA. For this purpose, the DNA to be examined is first transformed such that unmethylated cytosine is converted to uracil while 5-methylcytosine remains unchanged. Subsequently, the transformed DNA is amplified in the presence of a pair of real-time probes. For this, a probe is constructed, which is specific for the methylated or for the unmethylated state of the DNA, and a probe, which binds methylation-unspecifically to the amplificate. The ratio of the signal intensities of the probes or the CT values allows for the calculation of the degree of methylation of the examined DNA. The method according to the invention is suited particularly for the diagnosis and prognosis of cancer and other diseases associated with a change in the methylation status, as well as, prediction of adverse for side-effects of pharmaceuticals.

21 Claims, 10 Drawing Sheets

(56) References Cited

OTHER PUBLICATIONS

Pielberg: "A sensitive method for detecting variation in copy numbers of duplicated genes" Genome Res., vol. 13, No. 9, 2003, pp. 2171-2177.

Rand, K et al: "Conversion-specific detection of DNA methylation using real-time polymerase chain reaction (ConLight-MSP) to avoid false positives" Methods, vol. 27, No. 2, Jun. 2002, pp. 114-120.

Shifman: "Quantitative technologies for allele frequency estimation of SNPs in DNA pools", Mol. Cell. Probes, vol. 16, No. 6, 2002, pp. 429-434.

Trinh, B et al: "DNA methylation analysis by MethyLight technology" Methods, vol. 25, No. 4, Dec. 2001, pp. 456-462.

Weber: "A real-time polymerase chain reaction assay for quantification of allele ratios and correction of amplification bias" Anal. Biochem., vol. 320, No. 2, 2003, pp. 252-258.

Zeschnigk: "A novel real-time PCR assay for quantitative analysis of methylated alleles (QAMA): analysis of the retinoblastoma locus" Nucleic Acids Res., vol. 32, No. 16, 2004, p. E125.

* cited by examiner

METHOD FOR THE QUANTIFICATION OF METHYLATED DNA

BACKGROUND OF THE INVENTION

The present invention concerns a method for the quantification of methylated cytosine positions in DNA. 5-methylcytosine is the most commonly modified base in the DNA of eukaryotic cells. It plays an important biological roll in transcriptional regulation, genetic imprinting, and tumorogenesis among other things (for overview: Millar et al.: Five not four: History and significance of the fifth base. In: The Epigenome, S. Beck and A. Olek (eds.), Wiley-VCH Verlag Weinheim 2003, S. 3-20). The identification of 5-methylcytosine is particularly of considerable interest for cancer diagnosis. Detection of methylcytosine is, however, difficult, since cytosine and methylcytosine exhibit the same base-pairing behavior. Conventional DNA-analysis methods based on hybridization are, thus, not applicable. The current methods for methylation analysis operate based on two distinct principles. In one case, methylation-specific restriction enzymes are used, and in another, selective chemical conversion takes place of unmethylated cytosine into uracil (so-called: bisulfite-treatment, see also: DE 101 54 317 A1; DE 100 29 915 A1). The enzymatic or chemically treated DNA can be then in most cases amplified and is analyzed using different methods (for an overview: WO 02/072880 P 1 ff; Fraga and Estella: DNA methylation: a profile of methods and applications. Biotechniques. 2002 September; 33(3): 632, 634, 636-49.). For sensitive analysis, the chemically treated DNA is typically amplified using a PCR method. A selective amplification only of the methylated (or in the reverse approach: unmethylated) DNA can be ensured through the use of methylation specific primers or blockers (so-called methylation sensitive PCR/MSP or "Heavy Methyl method", compare: Herman et al.: Methylation-specific PCR: a novel PCR assay for methylation status of CpG islands. Proc Natl Acad Sci USA. 1996 Sep. 3; 93(18): 9821-6 Cottrell et al.: A real-time PCR assay for DNA-methylation using methylation-specific blockers. Nucl. Acids. Res. 2004 32: e10). On the other hand, it is also possible to first amplify the DNA in a methylation-specific manner and then to analyze the amplificates using methylation-specific probes (for overview: Trinh et al.: DNA methylation analysis by MethyLight technology. Methods. 2001 December; 25(4):456-62). The so-called PCR methods are also applicable as real-time PCR variations. This permits the detection of the methylation status directly during the course of the PCR without the necessity of a subsequent analysis of the product ("MethyLight"—WO00/70090; U.S. Pat. No. 6,331,393; Trinh et al. 2001, a.a.o.).

A quantification of the degree of methylation is necessary for several applications: for instance, for classification of tumors, for prognostic statements, or for the predictions of pharmaceutical side-effects. There are diverse methods known for the quantification of the degree of methylation. In part, an amplification, thereby, is first performed when using for instance, Ms-SNuPE, hybridization on microarrays, hybridization assays in solution or directly in bisulfite sequencing (for overview: Fraga and Estella 2002, a.a.o.). A problem exists within this "end point analysis" and that is, among other things, the amplification can occur non-uniformly due to product constraints, enzyme instability, and decreases in concentration of reaction components. A correlation between the amount of amplificate and the amount of DNA inserted is not always a given. The quantification is thereby error-prone (compare: Kains: The PCR plateau phase—towards an understanding of its limitations. Biochem. Biophys. Acta 1494 (2000) 23-27). Threshold-value analysis based on real-time PCR determines the quantity of an amplificate not at the end of the amplification but in the exponential phase of the amplification. It is assumed in this method that the amplification efficiency is constant in the exponential phase. The so-called threshold value Ct is the number of PCR cycles required before the signal in the exponential phase of the amplification is for the first time greater than the background noise. The absolute quantification is carried out then by comparing the Ct values of the examined DNA with the Ct values of the standards (compare: Trinh et al. 2001, a.a.o.; Lehmann et al.: Quantitative assessment of promoter hypermethylation during breast cancer development. Am J Pathol. 2002 February; 160(2):605-12). A problem, however, exists with the Ct analysis and that is, with high DNA concentrations only a low resolution can be achieved. The same is true when high degrees of methylation are to be investigated using PMR values (compare to PMR values: Eads et al., CANCER RESEARCH 61, 3410-3418, Apr. 15, 2001.). Additionally, this type of Ct analysis is also necessary for the amplification of a reference gene such as the β-actin gene (compare: Trinh et al 2001, a.a.o.).

Recently, a method for the quantification of methylation analysis has been described where the bisulfite-converted DNA is amplified and detected using both methylation-specific, real-time probes ("QM"-Assay). Thereby, one of the probes is specific for the methylation state, while the other probe is specific for the unmethylated state. Both the probes carry different fluorescent dyes. Within particular PCR cycles, a quantification of the degree of methylation can then be performed based upon, for example, the ratio of signal intensities of both probes or the Cts of the fluorescence channels (compae: European patent application: 04 090 213.2; Lehmann and Kreipe: Real-time PCR-based assay for quantitative determination of methylation status. Methods Mol Biol 2004; 287:207-18; Zeschnigk et al.: A novel real-time PCR assay for quantitative analysis of methylated alleles (QAMA): analysis of the retinoblastoma locus. Nucleic Acids Res. 2004 Sep. 7; 32(16):e125.)

In the following is another real-time PCR method described for the quantification of methylated DNA. Here, the bisulfite-treated DNA is likewise amplified and using both real-time probes, detected. In contrast to the method described above, here, however, only one of the probes is specific for the methylated (or the unmethylated) state. The other probe is methylation-specific. With help from both these probes, it is possible to carry out a simple quantification of cytosine methylation according to the invention.

A principle difference exists between the method according to the invention and the well-known Lightcycler method as given in the following: In the Lightcycler method, two oligonucleotide probes are employed, which hybridize to the amplificate spatially near each other. Through an energetic interaction (FRET) between both the probes, a generated fluorescent signal is subsequently detected. In the Lightcycler method, both the probes can only be detected together and not indepently of each other. In contrast, both probes, in the method according to the invention, are tagged with a dye, which permits the independent detection of each probe. As a result, two signals with two different expression qualities are generated: in that, one signal represents the total DNA, and the other signal is specific for the methylated/unmethylated DNA. The degree of methylation can be determined then from the ratio of both signals at the examined position. In an especially preferred embodiment of the method according to the invention, elements from the Lightcycler and the Taqman technologies are combined. This allows for a very efficient quantification.

Due to the known special biological and medical significances of cytosine methylation and due to the abovementioned disadvantages of the state of the art, there exists a great technical need for the development of an efficient method for the quantification of methylation analysis. The method according to the invention makes such a method available and with that, demonstrates an important technical improvement.

DESCRIPTION

The method according to the invention is suited preferably, but not exclusively, for the methylation analysis of DNA. For methylation analysis, the DNA is first chemically or enzymatically transformed, preferably through a bisulfite conversion. The principle of the invention consists thereof that an amplification is performed in the presence of a pair of real-time probes. The probes hybridize on the same amplificate at different positions.

In one embodiment, one of the probes binds in a methylation-specific manner to a methylation position, while the other probe binds to the amplificate independent of the amplificate's methylation status. In contrast to the Lightcycler method, at least one of the probes is detectable independent of the others. Subsequently, the signal of the probes is measured. The ratio between the specific probes and the unspecific probes permits the determination of the degree of methylation of the examined DNA. The calculation can be carried out over different computation methods, for instance, over signal intensities or Ct values.

In addition to the quantification of DNA, the method according to invention can be implemented for further applications in methylation analysis. If two methylation-specific probes are used, which bind to different CpG positions on the DNA, the invention allows for the measuring of both methylation positions relative to each other.

Moreover, a simultaneous examination of mutations or polymorphisms and methylations is possible, if a probe is used, which is specific for the mutation/polymorphism, and another probe, which is specific for a methylation status.

Furthermore, the method according to the invention is applicable outside of methylation analysis. A bisulfite conversion is, in this case, unnecessary. Thus, single nucleotide polymorphisms (SNP) for instance can be quantified or a different SNP can be measured relative to each other. Additionally, the method according to the invention can be applied for the quantification of allele-specific gene expression or for the examination of imprinting.

Especially preferred are embodiments where both real-time probes can interact with each other. Thus, an especially rapid and effective quantification is possible.

The method according to the invention is suited particularly for methylation analysis. A preferred embodiment of the invention is a method for the quantification of cytosine methylation that is characterized by the following steps:
  a) the DNA to be examined is transformed such that 5-methylcytosine remains unchanged while unmethylated cytosine is converted to uracil or another base, which can be distinguished from cytosine in its base-pairing behavior,
  b) the converted DNA is amplified in the presence of two real-time probes, whereby one of the probes is specific for either the methylated or the unmethylated state of the examined DNA, while the other probe is methylation-unspecific,
  c) the extent to which the amplification has proceeded is determined through detection of the hybridized probes,
  d) the degree of methylation of the examined DNA is ascertained with help from the signals.

In the first step of this embodiment, the DNA to be examined is transformed with a chemical or with an enzyme such that 5-methylcytosine remains unchanged while unmethylated cytosine is converted to uracil or another base, which can be distinguished from cytosine in its base-pairing behavior. Thereby, the DNA to be examined can stem from different sources depending on whether the question comes from the diagnostic or scientific research branch. For diagnostic questions, tissues preferably serve as the source material, but also possible are body fluids in particular serum. It is also possible to use DNA from sputum, stool, urine or spinal fluid. Preferably, the DNA is first isolated form a biological sample. The DNA extraction is carried out using standard methods, for instance, from blood using Qiagen UltraSens DNA Extraction Kit. The isolated DNA can then be fragmented, for example, through reaction with restriction enzymes. The reaction conditions and the enzymes to be considered are known to a person of skill in the art and are given, for instance, in the accompanying manufactures' protocols. Subsequently, the DNA is chemically or enzymatically converted. Preferably, a chemical reaction is carried out using bisulfite. The bisulfite conversion in its different variations is known to a person of skill in the art (see for example: Frommer et al.: A genomic sequencing protocol that yields a positive display of 5-methylcytosine residues in individual DNA strands. Proc Natl Acad Sci USA. 1992 Mar. 1; 89(5):1827-31; Olek, A modified and improved method for bisulphite based cytosine methylation analysis. Nucleic Acids Res. 1996 Dec. 15; 24(24): 5064-6.; DE 100 29 915; DE 100 29 915). Especially preferred, the bisulfite conversion is performed in the presence of denaturing solvents and radical scavengers (compare.: DE 100 29 915).

Exceptionally preferred embodiments of the bisulfite conversion using of n-alkylenglycol compounds, in particular from Diethylenglycoldimethylether (DME) or from dioxan or dioxan derivatives, as well as, by applying special temperature profiles and purification methods, are described in the PCT application PCT/EP 2004/011715. In another preferred embodiment, the DNA is not chemically, but enzymatically converted. This, for example, is conceivable through the use of cytidine deaminases, which reacts quicker with unmethylated cytidine than with methylated cytidine. An appropriate enzyme has been identified recently (Bransteitter et al.: Activation-induced cytidine deaminase deaminates deoxycytidine on single-stranded DNA but requires the action of RNase. Proc Natl Acad Sci USA. 2003 Apr. 1; 100(7):4102-7).

In the second step of the method according to the invention, the converted DNA is amplified in the presence of a pair of real-time probes, whereby one of the probes is specific for either the methylated or the unmethylated state, while the other probe is methylation-unspecific. The first probe, in the following, is identified as methylation-specific probe. Preferably, an amplification is, thereby, carried out using an exponential amplification method, especially preferred is the use of PCR. For the amplification, primers are used, which are specific for the chemical or enzymatic converted DNA. In a preferred embodiment, methylation-unspecific primers are, thereby, employed; that is, primers, which do not have CG- or, as the case may be, methylation-specific TG- or CA-dinucleotides. With these primers, an uniform amplification of methylated and unmethylated DNA occurs. In another preferred embodiment, methylation-specific primers are used;

thus, primers, which have CG or methylation-specific TG- or CA-dinucleotide. Thus, it is possible to amplify large methylation-specific sequences, and at the same time, quantify particular cytosine positions within the sequence using the method according to the invention. The design of the methylation-specific and methylation-unspecific primers and the PCR reaction conditions are from the state of the art (compare for example: U.S. Pat. No. 6,331,393; Trinh et al 2001, a.a.o.).

The amplification takes place in the presence of a pair of different probes, whereby one of the probes is methylation-specific, while the other probe is specific for the unmethylated state of the DNA. The methylation-specific probe carries accordingly at least one Cpg (in the case of the detection of methylated DNA), a specific TG- or CA-dinucleotide (in the case of detection of unmethylated DNA). Preferably, the probes carry three specific dinucleotides. The methylation-unspecific probes do not contain the corresponding dinucleotides. The probes bind preferably to different positions on the DNA. Preferably, both probes have similar melting temperatures.

The probes concerned in this case are real-time probes. The term, real-time probes, refers to probes that permit the detection of the amplificate during the amplification procedure. The different real-time PCR variations are known to the person of skill in the art, such as, Lightcycler-, Taqman-, Sunrise-, Molecular Beacon-, or Eclipse-Probes. The particulars on the construction and detection of these probes are a part of the state of the art (compare: U.S. Pat. No. 6,331,393 for further information). Thus, the design of the probes can be carried out, for instance, over the "PrimerExpress" software from Applied Biosystems (for Taqman-Probes) or over MGB Eclipse Design software from Epoch Biosciences (for Eclipse-Probes).

Preferably both probes carry different dyes, so that it is possible to detect them separately. The amplification takes place preferably together with both probes in one tube; thus, the reaction conditions are identical for both probes. It is, however, not absolutely necessary that both probes carry distinct labels. It is, on the other hand, also possible to perform the amplifications in different tubes. Through this, the spurious interactions between the fluorescent dyes are avoided.

In a preferred embodiment, the amplificates bind to different locations on the same strand of the amplificate. In another preferred embodiment, each probe binds respectively to another strand of the amplificate (see below in detail).

If the probes bind to the same strand, then the dyes of both probes interact with each other in a proffered embodiment. Thus, a very efficient quantification is possible. These especially preferred embodiments are described in detail below.

In the third step of the method according to the invention, the extent to which the amplification has proceeded is determined at various time points. This is carried out through detection of the probes bound to the amplificate. The detection of hybridization takes place during each amplification cycle. The detection occurs independently of the deployed probes according to the state of the art.

In the fourth step of the method according to the invention, the degree of methylation of the examined DNA is ascertained with help from the detected signals.

The determination of the degree of methylation can be done in different ways. In a preferred embodiment, the probes possess comparable lengths and melting temperatures. Preferably, the degree of methylation of the examined DNA is determined from the ratio of the signal intensities of both probes. This can be carried out, for instance, using the following formula:

$$M = 100 \cdot I_{CG}/I_{UN}$$

In the formula, the $I_{CG}$ represents the signal intensity of methylation-state-specific probe and $I_{IN}$ represents the signal intensity of the methylation-unspecific probe.

Especially preferred, from the signal intensities, ratios are formed during a PCR cycle in the exponential amplification phase of the PCR. Preferably, a calculation is carried out close to the cycle during which the Amplification reaches its maximal slope. This equals the point of inflection of the fluorescence intensity curves or the maximum of the first derivation.

The calculation is carried out at a time point, which lies preferably up to five cycles before or after the point of inflection, especially preferred up to two cycles before or after the point of inflection, and exceptionally preferred up to one cycle before or after the point of inflection. In the best embodiment, the calculation takes place directly at the point of inflection.

The determination of the point of inflection is carried out preferably over the first derivation of the fluorescence intensity curves. Preferably, the derivations are first subjected to smoothing ("Spline", compare: Press, W. H., Teukolsky, S. A., Vetterling, W. T., Flannery, B. P. (2002). Numerical Recipes in C. Cambridge: University Press; Chapter 3.3.).

In another preferred embodiment, the calculation of the degree of methylation is carried out not through the ratio of signal intensities but through the ratio of threshold values at which a certain signal intensity is exceeded, for instance by Ct values (see above). The determination of Ct values is from the state of the art (compare: Trinh et al, a.a.o., 2002). The degree of methylation can then be determined through the use of the following formula: Degree of methylation=$100/(1+2^{\Delta aCt})$.

Moreover, it is conceivable to use other criteria for the calculation of the degree of methylation, for example, the area under the fluorescence curves or the maximum slope of the curves.

A quantification through the above described method is especially possible when the assay conditions in this regard have been optimized beforehand. An optimization is carried out with different methylation standards (for example with 0%, 5%, 10%, 25%, 50%, 75% and 100% degree of methylation). As standard, DNA is preferably used, which covers the entire genomic DNA or covers a representative portion thereof. One acquires the different degrees of methylation through a proportionate mixture of methylated and not methylated DNA. The production of methylated DNA is relatively simple through the use of SssI methylase. This enzyme transforms in the sequence context "CG" all unmethylated cytosines into 5-methylcytosine. As completely unmethylated DNA, sperm DNA can be used, which has only a low degree of methylation (compare: Trinh et al. 2001, a.a.o.). Preferably, however, the production of not methylated DNA is performed using the so-called genome-wide amplification (WGA—whole genome amplification, for overview: Hawkins et al.: Whole genome amplification—applications and advances. Curr. Opin. Biotechnol. 2002 February; 13(1): 65-7).WGA). In this case, a large portion of the genome is amplified using "Random" or degenerated primers. Since only unmethylated cytosine nucleotides are available in the amplification, completely unmethylated DNA results after many amplification cycles. Preferred, thereby is "Multiple Displacement Amplification" using φ29 polymerase (MDA, compare: Dean et al. 2002 a.a.o.; U.S. Pat. No. 6,124,120). Appropriately manufactured DNA is available through different commercial vendors ("GenomiPhi" from Amersham Biosciences, www4.amershambiosciences.com; "Repli-g" from Molecular Staging, www.molecularstaging.com). The manufacture of methylation standards is described in detail in the European patent application 04 090 037.5 (application date: 5 Feb. 2004; Applicant: Epigenomics AG). The quotient is formed using the signals that were detected from the methylated state, and the sum of the signals, which are detected from the methylated and unmethylated state. Thereby, one acquires the measured methylation rate. When one plots these (the measured methylation rate) over the theoretical methylation ratios (according to the portion of methylated DNA in the defined mixtures) and ascertains the regression, which goes through the measuring point, one acquires a calibration curve. A calibration is performed preferably with different quantities of DNA, for instance with 0.1; 1 and 10 ng DNA per sample.

Assays are especially suited for the quantification via the method according to the invention, when the calibration curves for the time point of the exponential amplification preferably intercept the y-axis at zero. Proximate methylation states should be discerned using a high Fischer score (preferably over 1, especially preferred over 3). Furthermore, it is advantageous when they possibly have a low y-axis intercept and a high Fischer score (preferably over 1, especially preferred over 3). Furthermore, it is advantageous when the curves have a slope and a regression value close to 1.

The assays can, in this regard, be optimized using variations in primers, probes, temperature programs and further reaction parameters through standardization trials.

Further Preferred Embodiments for Methylation Analysis

As stated above, the method according to invention is suited particularly for the determination of the degree of methylation of DNA; by using a methylation-specific probe and an unspecific probe, respectively, the methylated DNA and the total DNA is determined, respectively. The invention is, however, not limited to this use. In fact, the inventive concept allows for the formulation of much more as given in the following: The amplification of chemically converted DNA is detected using a pair of real-time probes. Thereby, the probes bind within the amplificates at two different positions. The probes carry dyes, which permits the independent detection of at least one of both probes. The proportion of the sequences, to which the probes hybridize, can be concluded from the ratio of the signals. Thereby, it is preferred that if one of the probes is specific for a methylation status, then the other probe binds methylation-unspecifically to the amplificate. Moreover, it is also possible to identify the ratio of distinct, adjacent cytosine positions to each other. In this case, a probe is used, which binds methylation-specifically to the first position, and a second probe, which binds to the second position methylation-specifically. Thereby, it is possible that both probes are specific for the methylated state. It is also possible that both probes are specific for the unmethylated state. It is also conceivable that one of the probes is specific for the methylated state and the other probe is specific for the unmethylated state. Finally, it is also possible that the probes bind to different strands of the amplificate. In this embodiment, one should see that the probes are not complementary to each other, since an accumulation of probe-dimers may arise. If the probes have, however, an overlap of a very few bases, it is conceivable to detect the same position on one strand as well as on the other strand (for example, on one strand, the methylated position, and on the other strand, the unmethylated position). For this embodiment, the same position on two different strands is, thus, viewed as distinct positions. A quantification can, in this case, be performed as described at length in the European patent application 04 090 213.2.

Accordingly, this embodiment of the method according to invention is described as follows:

The method for the analysis of cytosine methylation, characterized in that the following Steps are performed:
a) the DNA to be examined is transformed such that 5-methylcytosine remains unchanged while unmethylated cytosine is converted to uracil or another base, which can be distinguished from cytosine in its base-pairing behavior,
b) the converted DNA is amplified in the presence of two real-time probes, whereby the probes are specific for either the methylated or the unmethylated state of different respective cytosine positions,
c) at different time points, the extent to which the amplification has proceeded is determined through detection of the hybridized probes,
d) the ratio of methylation of the two different positions are ascertained with help from the signals.

Thereby, the steps a)-d) are performed basically as described above. The above-described embodiment shall be referred to explicitly. Accordingly, the bisulfite conversion is performed preferably first, and that is carried out, especially preferred, in the presence of denaturing solvents and a radical scavenger (compare: DE 100 29 915). Exceptionally preferred, the bisulfite conversion is carried out using n-alkylenglycol compounds, in particular from Diethylenglycoldimethylether (DME) or dioxan or dioxan derivatives, as well as, by using special temperature profiles and purification methods (PCT/EP 2004/011715).

In the second step of the method according to the invention, the converted DNA is amplified in the presence of a pair of real-time probes, whereby both probes are methylation-specific; that is, they are specific either for the methylated or the not methylated state of DNA. Thus, both the probes are specific for different cytosine positions, respectively.

Especially preferred, the amplification is carried out using PCR. For the amplification, primers are used, which are specific for the converted DNA. In a preferred embodiment, methylation-unspecific primers are used at the same time. In another preferred embodiment, methylation-specific primers are used (see above). The design of the methylation-specific and methylation-unspecific primers and the PCR reaction conditions are from the state of the art (compare, for example: U.S. Pat. No. 6,331,393; Trinh et al 2001, a.a.o.).

The amplification takes place in the presence of a pair of different methylation-specific probes. The probes carry accordingly at least one CpG (when examining methylated DNA) or a specific TG-, or CA-dinucleotide (when examining unmethylated DNA). Preferably, the probes carry three specific dinucleotides. Preferably, both probes have similar melting temperatures.

The probes concerned in this case are real-time probes. The real-time probes refer to probes that permit the detection of the amplificate during the amplification procedure. Different real-time PCR variations are familiar to a person skilled in the art, for example, Lightcycler, Taqman, Sunrise, Molecular Beacon or Eclipse probes. Particulars on constructing and detecting the probes are a part of the state of the art (compare: U.S. Pat. No. 6,331,393 for further information). Thus, the design of the probes can be carried out, for instance, over the "PrimerExpress" software from Applied Biosystems (for Taqman-Probes) or over MGB Eclipse Design software from Epoch Biosciences (for Eclipse-Probes).

Preferably both probes carry distinct dyes, so that it is possible to detect at least one of the two probes independently of the other. The amplification takes place preferably together with both probes in one tube; thus, the reaction conditions are identical for both probes. It is, however, not absolutely necessary that both probes carry distinct labels. It is, on the other hand, also possible to perform the amplifications in different tubes. Through this, the spurious interactions between the fluorescent dyes are avoided.

In an especially preferred embodiment, the dyes of both the probes interact with each other. Thus, a very efficient quantification is possible. These especially preferred embodiments are described in detail below.

In the third step of the method according to the invention, the extent to which the amplification has proceeded is determined at various time points. This is carried out through a detection of the amplificate-bound probes. The detection of hybridization takes place during each amplification cycle. The detection takes place regardless of the probes being used, according to the state of the art.

In the fourth step of the method according to the invention, the percentage of methylation in the two different positions is ascertained with help from the detected signals.

The calculation can be done in different ways as described in detail above. In a preferred embodiment, the calculation is performed via the ratio of the sequence intensities. Especially preferred, this takes place during a PCR cycle in the exponential amplification phase of the PCR. Preferably, a calculation is carried out close to the cycle where the amplification reaches its maximum slope. This equals the point of inflection of the fluorescence intensity curves or the maximum of the first derivation. The calculation takes place, thereby, near a time point, which lies preferably up to five cycles before or after the point of inflection, especially preferred up to two cycles before or after the point of inflection and exceptionally preferred up to one cycle before or after the point of inflection. In the best embodiment, the calculation takes place directly at the point of inflection. In case the points of inflection of both curves lie in the different cycles, the calculation takes place preferably at the point of inflection of the curve, which exhibits the highest signal at this time point. The point of inflection is determined as described above.

In another preferred embodiment, the calculation of the degree of methylation is carried out not through the ratio of signal intensities but through the ratio of threshold values at which a certain signal intensity has been exceeded, for instance by Ct values (see above). Moreover, it is conceivable to use other criteria for the calculation of the degree of methylation, for example, the area under the fluorescence curves or the maximum slope of the curves.

A quantification via the above described methods is especially possible, when the assay conditions, in this regard, were optimized beforehand (see above). Assays are especially suited for the quantification via the method according to the invention, when the calibration curves for the time point of the exponential amplification have preferably a value of zero at the y-axis intercept. Proximate methylation states should be discerned using a high Fischer score (preferably over 1, especially preferred over 3). Furthermore, it is advantageous when they possibly have a low y-axis intercept and a high Fischer score (preferably over 1, especially preferred over 3). Furthermore, it is advantageous when the curves have a slope and a regression value close to 1 (see above).

Further Preferred Embodiments for Simultaneous Examination of Methylation and Mutations/SNP As performed above, the method according to the invention is suited particularly for methylation analysis. Furthermore, a simultaneous analysis of methylation and mutations or polymorphisms can be set up. Thereby, the DNA is bisulfite-converted and afterwards, amplified with the help of a pair of real-time probes. One of the probes is, thereby, specific for a particular methylation position while the other probe is specific for a SNP position. Accordingly, this embodiment of the invention's method can be described as follows:

The method for the simultaneous analysis of cytosine methylation and mutations/SNP, characterized in that the following steps are carried out:
 a) the DNA to be examined is transformed such that 5-methylcytosine remains unchanged while unmethylated cytosine is converted to uracil or another base, which can be distinguished from cytosine in its base-pairing behavior,
 b) the converted DNA is amplified in the presence of two real-time probes, whereby one of the probes is specific for either the methylated or the not methylated state of DNA, and the other probe is specific for a mutation/polymorphism,
 c) at various time points, the extent to which the amplification has proceeded is determined through detection of the hybridized probes,
 d) the ratios between methylation and the mutation/polymorphism is ascertained with help from the signals.

Thereby, the steps a)-d) are performed basically as described above. The above described embodiment will be referred to explicitly. There should be preferably probes included from which at least one can be detected independently from the others.

Further Preferred Embodiments for Use Outside of Methylation Analysis

In a further embodiment of the method according to the invention, SNP or polymorphism are quantified. The quantification takes place basically as has been described for methylation analysis above. A bisulfite conversion is, however, not necessary. The DNA to be examined is amplified in the presence of a pair of real-time probes, whereby a probe is specific for the mutation/polymorphism, and the other probe binds to the mutations/SNP-unspecific of the constructed amplificate. The mutation/polymorphism can be quantified from the relation of the signals between a specific probe and an unspecific probe. The calculation can be carried out via different calculation methods, for instance, via signal intensities or Ct values. To the above-described embodiment shall be referred to explicitly. Accordingly, this embodiment is described as follows:

A method for quantification of mutations/SNP, characterized in that the following steps are performed:
 a) the DNA to be analyzed is amplified in the presence of two real-time probes, whereby one of the probes is specific for either the methylated or the unmethylated state of the DNA, and the other probe is specific for a mutation/polymorphism,
 b) at various time points, the extent to which the amplification has proceeded is determined through detection of the hybridized probes,
 c) the percentage of a mutation/polymorphism in the examined DNA is ascertained with help from the signals.

Thereby, the steps a)-c) are performed basically as described above. The above described embodiment shall be referred to explicitly. There are probes included preferably from which at least one can be detected independently from the others.

Especially preferred, this embodiment can be applied to examine single nucleotide polymorphism (SNP) from pooled samples. Pooling of samples is for different questions meaningful, for instance for the identification of genes, which take part in the development of complex diseases (compare: Shifman et al.: Quantitative technologies for allele frequency estimation of SNPs in DNA pools. Mol Cell Probes 2002 December; 16(6):429-34).

Moreover, the different mutations/SNP positions can be measured with one another according to the invention. In that case, two probes, which are specific for a mutation/polymorphism, are used. For the calculation, what was said above applies for the determination of different methylation positions.

According to the same principle, a gene duplication can also be examined (compare: Pielberg et al.: A sensitive method for detecting variation in copy numbers of duplicated genes. Genome Res 2003 September; 13(9):2171-7).

A further use of the method according to the invention is the examination of mutations in microorganisms. Thus, it can be determined which proportion of a sample stems from a wildtype or a mutant strain. Such an application is meaningful for therapeutic decisions (compare, for example: Nelson et al.: Detection of all single-base mismatches in solution by chemiluminescence. Nucleic Acids Res 1996 Dec. 15; 24(24):4998-5003).

Accordingly, a method for determining which proportion of a sample stems from a wildtype microorganism and which proportion stems from a mutant is also inventive and is characterized in that
  a) the sample to be examined is amplified in the presence of a pair of real-time probes, whereby one of the probes is specific for the wildtype strain, while the other probe binds to the amplificate independent of the mutation/polymorphism,
  b) at various time points, the extent to which the amplification has proceeded is determined through detection of the hybridized probes,
  c) it is concluded, which strain is present in the sample and the proportion of each strain.

Use of the Method According to the Invention for Analysis of Allele-specific Gene Expression A further preferred embodiment of the method according to the invention is the examination of allele-specific gene expression (compare to allele-specific gene expression: Lo et al.: Allelic variation in gene expression is common in the human genome. Genome Res. 2003 August; 13(8):1855-62; Weber et al.: A real-time polymerase chain reaction assay for quantification of allele ratios and correction of amplification bias. Anal Biochem 2003 Sep. 15; 320(2):252-8).

A method for quantification of allele-specific gene expression, characterized in that:
  a) the RNA to be examined is reverse transcribed into cDNA,
  b) the cDNA is amplified in the presence of a pair of real-time probes, whereby one probe is allele-specific, while the other probe is allele-unspecific
  c) at various time points, the extent to which the amplification has proceeded is determined through detection of the hybridized probes,
  d) a quantification of allele-specific gene expression is performed from the generated signals.

In the first step of this embodiment, the RNA to be examined is reverse transcribed. Corresponding methods are known in the state of the art (compare: Lo et al. 2003, a.a.o.). Commonly the RNA is first isolated. For this, diverse commercially available kits can be used (for example, Micro-Fast Track, Invitrogen; RNAzol B, Tel-Test). The cDNA is generated subsequently with the help of a commercially available reverse transcriptase (for example from Invitrogen).

Especially Preferred Embodiment of the Method According to the Invention Through Interacting Probes In an especially preferred embodiment, the method according to the invention is so configured that both the real-time probes, being used, interact with each other in a special form through their dyes. The conventional Lightcycler and Taqman methods already utilize an interaction between distinct dyes. In the Taqman method, a probe is used that carries a dye as well as a quencher. In the course of the amplification, the probe is digested. As a result, the quencher is separated from the dye, so that a signal can be detected. With the Lightcycler method, in contrast, two probes hybridize in direct proximity to each other, whereby the dye of one of the probes is excited through an energy transfer (FRET). The method according to the invention combines now both the principles and permits in particular a very efficient analysis of cytosine methylation.

Preferably, a Taqman and a Lightcycler probe are used at the same time, which hybridize directly next to each other. Thereby, the fluorescent dyes of the Taqman probe serve as donors to excite the Lightcycler probe. Therefore, at least two distinct signals are generated; the signal of the Taqman probe during its degradation and the signal of the Lightcycler probe during hybridization near the Taqman probe. During the conventional Lightcycler method, only one signal is generated, in contrast.

In an especially preferred embodiment, the Taqman probe, thereby, is constructed in a particular form: the fluorescent dye lies typically at the 5'end and the quencher at the 3'end. According to the invention, the dye is positioned instead at the 3'end. The quencher, which is localized in the 5' direction to the dye, lies approximately in the middle or at the 5'end of the probe. The sequence of the Taqman probe is preferably methylation-unspecific; that is, it contains neither a CG-dinucleotide nor a methylation-specific TG or CA dinucleotide. Thus, the Taqman probe hybridizes to the bisulfite-treated DNA independent of the original methylation status and therefore, is used to determine the total amount of bisulfite-treated DNA. At the same time, a Lightcycler probe is used where the sequence is methylation-specific; that is, it contains at least one methylation-specific CG-, TG-, or CA-dinucleotide. The Lightcycler probe serves to measure the methylated or unmethylated portion of the DNA. The Lightcycler probe is constructed such that it binds to the amplificate near the Taqman probe. The dye, which is located at the 3'end of the Taqman probe, can then activate the dye of the Lightcycler probe through FRET. The signal of the Taqman and Lightcycler probes can then be measured on different channels. The degree of methylation at the examined position can then be determined from the ratio of both the signals. This embodiment has the advantage that the specific methylation signal can be generated through the Lightcycler probe only when the methylation-unspecific signal was already produced through the Taqman probe. This results in an increased specificity of methylation detection.

This especially preferred embodiment of the method according to the invention for the quantification of cytosine methylation can be described through the following steps:
  a) the DNA to be examined is transformed such that 5-methylcytosine remains unchanged while unmethylated cytosine is converted to uracil or another base, which can be distinguished from cytosine in its base-pairing behavior, b) the converted DNA is amplified in the presence of two real-time probes, whereby at least one of the probes can be detected independently, and whereby one of the probes is specific for either the methylated or the unmethylated state of the DNA to be examined, while the other probe is methylation-unspecific, c) the methylation-unspecific probe carries a donor dye, which activates the dye of the methylation-specific probe through FRET, as soon as they hybridize near each other on the amplificate, d) at various time points, the extent to which the amplification has proceeded is determined through detection of the hybridized probes, e) the degree of methylation of the DNA to be examined is ascertained with help from the signals.

Sample preparation, bisulfite-conversion, amplification and analysis of the signals are performed, thereby, as described above in detail.

Preferably in step c), a Taqman probe is used as a methylation-unspecific probe where the dye is located at the 3'end and the quencher is in the 5' direction from the dye. Further preferred, a Lightcycler probe is used as a methylation-specific probe where the dye is activated by the dye from the Taqman probe.

This especially preferred embodiment of the method according to the invention can be applied to determine the ratio of different methylation positions to each other. This application has been described already in general above. To this description reference is made. In this especially preferred embodiment, two methylation-specific probes are then used, whereby one of the probes activates the other through FRET.

This especially preferred embodiment of the method according to the invention can be applied to examine simultaneously mutations/polymorphisms and methylation as well as outside of methylation analysis, for example, for the quantification of polymorphism/mutations or for the analysis of allele-specific gene expression. These applications have been described already in detail above. In this especially preferred embodiment, two probes are used, which interact with each other as described above, for instance, in a Lightcycler-Taqman combination.

Special Embodiment for the Examination of Allele-specific Imprinting

A special embodiment of the method according to the invention demonstrates the use of a FRET system consisting of three probes. Thereby, two methylation-specific probes bind in direct proximity to a SNP-specific probe so that a signal is generated through Fluorescence Resonance Energy Transfer. In this embodiment, the SNP-specific probe carries the donor dye, and both methylation-specific probes carry two different acceptor dyes. A signal is only generated when the original DNA has the expected polymorphism, so that it can bind the SNP-specific donor probe. Depending on the methylation status, it excites the probe for methylated or unmethylated DNA. As described above, the signals can then be used to calculate the degree of methylation. This embodiment concerns an allele-specific "QM" assay. As already mentioned in the introduction, the QM assay is described at length in the European patent application 04 090 213.2. This application shall be once more referred to explicitly. In particular, the calculation method, mentioned in the application, can also be applied for the allele-specific QM assay. With the allele-specific QM assay, for example, methylation values can be assigned to one of the parental alleles when the DNA was obtained from the offspring, whose parents differ in the described polymorphisms. This embodiment is suitable especially for DNA methylation analysis in regions where a allele-specific imprinting is liable to be. With help from this embodiment, for example, methylation values can be assigned to a male or a female parental allele.

This embodiment for examination of allele-specific imprinting is described as follows:

a) the DNA to be examined is transformed such that 5-methylcytosine remains unchanged while unmethylated cytosine is converted to uracil or another base, which can be distinguished from cytosine in its base-pairing behavior, b) the converted DNA is amplified in the presence of two methylation-specific probes and a SNP-specific real-time probe, whereby one of the methylation-specific probes is specific for the methylated state of a particular cytosine position, and the other methylation-specific probe is specific for the unmethylated state of the DNA, and whereby the SNP-specific probe carries a donor dye, which activates the dye of the methylation-specific probe through FRET as soon as they hybridize next to each other, c) at various time points, the extent to which the amplification has proceeded is determined through detection of the hybridized probes, d) the degree of methylation of the DNA to be examined is ascertained with help from the signals.

Application of the Method According to the Invention

An especially preferred application according to the invention in particular for methylation analysis lies in the diagnosis and prognosis of cancer or other diseases associated with a change in the methylation status. To this belong among other things CNS-malfunction; symptoms of aggression or behavioral disorders; clinical, psychological and social consequences from brain impairment; psychotic disorders and personality disorders; Dementia and/or associated syndromes; cardiovascular disease, malfunction and impairment; malfunction, impairment or disease of the gastrointestinal tract; malfunction, impairment or disease of the lung system; damage, inflammation, infection, immune and/or convalescence; malfunction, impairment, or disease of the body as an abnormality in development processes; malfunction, impairment, or disease of the skin, muscle, connective tissue or skeletal tissue; endocrine or metabolic malfunction, impairment or disease; headaches, or sexual malfunction. The method according to invention is suited additionally for the prediction of adverse drug side effects and for distinguishing cell types or tissues or for the examination of cell differentiation.

Kits According to the Invention

Furthermore, a kit according to the invention for the implementation of the method according to invention consists of two primers, a polymerase and two real-time probes, as well as optionally, reagents necessary for PCR and/or bisulfite reagents.

At least one of the probes from the two real-time probes binds to a proven methylation-/SNP- or allele-specific position, while the other probe binds to methylation-/SNP- or allele-specific or methylation-/SNP- or allele-unspecific on the sequence to be examined. In contrast to the known Lightcycler method, there is at least one probe, which is detectable independently of the other. Preferably, the dyes of the probes interact with one another. Preferably, one of the probes is a Lightcycler probe and the other is a Taqman probe. Preferably, the Taqman probe is constructed such that the dye is located at the 3'end and the quencher is located in the 5' direction to the dye. Furthermore, a Lightcyler probe is used preferably as a methylation-specific probe where the dye is activated by the dye of Taqman probe.

EXAMPLES

Example 1

Dual-Color Real Time PCR for the Detection of Methylated DNA in the IGF2 Gene of Mouse with Simultaneous Detection of Total DNA via the Application of the Method According to the Invention In the present example, a Real Time PCR is carried out for the detection of methylated bisulfite-converted DNA. The chromosomal mouse DNA (Promega Corporation) is methylated genome-wide using SssI methyltransferase. Unmethylated control DNA is produced through genome-wide amplification using phi29 Polymerase (GenomiPhi-Kit, Amersham). Methylated and unmethylated DNA are treated with sodium bisulfite and subsequently, desulfonated with sodium hydroxide (method according to patent WO 2005/038051). Using bisulfite specific primer (SEQ ID NO: 1, SEQ ID NO: 2), a 161 bp long sequence of the IGF2 gene from mouse (SEQ ID NO: 5, NT_039437.4, nt909691-nt909851) is amplified with a Lightcycler system. The use of a 5'-fluorescence- und 3'-BHQ1-modified probes (SEQ ID NO: 3) serves to detect the total DNA in channel Ch1 (530 nm). Thereby, the signal is generated through the exonuclease activity of the polymerase, which hydrolizes the 5'end of the probe and with that releases fluorescent dye. The sequence of the Taqman probe would be chosen such that it contains no CG-dinucleotide and thus, binds to the entire DNA regardless of its methylation status.

The reaction comprises, furthermore, a second probe (SEQ ID NO: 4), which binds in direct proximity to the first probe (SEQ ID NO: 3) on the same DNA strand. It straddles 3 CpGs and serves to detect methylated DNA of the IGF2 sequence. The 3'end of the second probe (SEQ ID NO: 4) was modified with the Lightcycler dye LCred640 for detection with a wavelength of 640 nm. The simultaneous binding of the two probes, in the annealing phase of the PCR, excites a signal in the channel Ch2 (640 nm). In the experiment, 100 ng of unmethylated bisulfite-converted DNA was measured in channel Ch1 (530 nm) with a CT (cycle threshold) of 26,75. 1 ng of methylated DNA was detected in the same channel at CT 36,25 (FIG. 1). In channel Ch2, however, methylated DNA was detected exclusively with a CT of 36,25 (FIG. 2). All CTs are averages of two measurements (Table 2). In the following, the reaction conditions and results are described in detail.

The PCR reaction was carried out in the LightCycler in 20 µl reaction volumes and contained:
10 µl of Template-DNA
2 µl PCR buffer (Qiagen, containing 1.5 mM MgCl2)
0.25 mg/ml BSA (Sigma, non acetylated)
0.25 mM dNTPs each (dATP, dTTP, dGTP, CTP, Fermentas)
3.0 mM MgCl$_2$ (Qiagen)
0.30 µM Forward primer (SEQ ID NO: 1, TIB-MolBiol)
0.30 µM Reverse primer (SEQ ID NO: 2, TIB-MolBiol)
0.15 µM Probe1 (SEQ ID NO: 3, TIB-MolBiol)
0.15 µM Probe2 (SEQ ID NO: 4, TIB-MolBiol)
2 Units HotStarTaq Polymerase (Qiagen)

The temperature-time-profile was programed as follows:
Activation of polymerase: 15 min at 95°
55 temperature cycles: 10 sec at 95°
30 sec at 56° C.
10 sec at 72° C.

In conclusion, the reaction is cooled at 35° C. The analysis was performed with the SoFar software 1.1.1 (201 2005 Jochen Wilhelm).

TABLE 1

Sequences

| SEQ ID No | Name | Sequence |
|---|---|---|
| SEQ ID No: 1 | IGF2-b2-F | TtAtTGATGGTTGtTGGAtATtTt |
| SEQ ID No: 2 | IGF2-b2-R | aAaaCCTaCCTaCCCTCCTa |
| SEQ ID No: 3 | IGF2_Fluo | fluo-TGGttTtTtTGAAtTtTTTGAGtTtTTTG-BHQ1 |
| SEQ ID No: 4 | IGF2_Red | CGATtAGGGGACGATGACG-red640 |
| SEQ ID No: 5 | IGF2-amp | TtAtTGATGGTTGtTGGAtATtTtCGAAGAGGtTttttCGTGGGCGGGGTtTTTGGGTGGTAAtACGATtAGGGGACGATGACGTTTGGttTtTtTGAAtTtTTTGAGtTtTTTGGtAAG-tATGCGAtttCGGCGGGtACGtAG-GAGGGtAGGtAGGttTt |

The abbreviations represent:
Fluo = Fluoroscine,
red640 = LightCycler dye for 640 nm,
BHQ1 = BlackHoleQuencher1.
Lower case letters indicated cytosine positions, which are converted through bisulfite-conversion into uracil or subsequently, into thymine in PCR.

TABLE 2

In Real Time PCR measured CT values (threshold cycle)

| DNA | CT in channel Ch1 (530 nm) | CT in channel Ch2 (640 nm) |
|---|---|---|
| 1 ng methylated bisulfite-converted DNA | 36, 25 | 36, 25 |
| 100 ng unmethylated bisulfite-converted DNA | 26, 75 | — |
| Negative controls (water) | — | — |

Example 2

Allele-specific Quantitative Methylation Measurements Using Real Time PCR

The example describes the measurement of a proportion of methylated DNA in a region of the IGF2 gene of mouse using allele-specific QM assay. The QM assay technology (Patent PCT/EP2005/003793) is based on the collective amplification of methylated and unmethylated bisulfite-converted DNA in Real Time PCR, whereby the detection takes place with two distinctly labeled methylation-specific probes. The signals for methylated and unmethylated DNA are detected at different wavelengths and interpreted, according to the patented method (PCT/EP2005/003793). Using calibration of the measured values with defined DNA-mixtures of methylated and unmethylated DNA, the percentages of methylated DNA of the examined region are computed. The present example demonstrates that through the application of a second allele-specific probe (SEQ ID NO: 8 and SEQ ID NO: 9), measurement of methylation, at any one time, of one of the two alleles can be limited (FIG. 3). For this purpose, a strain-specific donor-probe was developed, which spans a polymorphism of a laboratory mouse strain (SD7) (SEQ ID NO: 9). It concerns a base substitution (SNPs single nucleotide polymorphism) at the positions nt9 09785 (T —>A) as well as nt909792 (T->G) the sequence NT_039437.4. The SD7-specific donor-probe hybridizes near the methylation-specific acceptor-probe (SEQ ID NO: 10, SEQ ID NO: 11) and excites a FRET signal (Fluorescence-Resonance-Energy-Transfer). Either the acceptor-probe for methylated DNA (SEQ ID NO: 10) or the acceptor-probe for unmethylated DNA (SEQ ID NO: 11) binds depending on the methylation status. The signals measured at different wave-lengths are analyzed according to the method of the QM assay. In this case, the degree of methylation, investigated, refers only to the DNA of the laboratory strain (SD7).

According to the same principle, a second assay was implemented for the methylation of the wildtype strain (BL6). The donor-probe (SEQ ID NO: 8, being used, binds thereby to the same position; however, it contains instead bases for the wildtype-specific strain at the polymorphism site.

Through the controlled crossing of the wildtype strain (BL6) with the laboratory strain (SD7), heterozygotic progeny are generated whose chromosomes can be distinguished on the basis of the specified polymorphisms and can be assigned to the respective parental strain and with that, the gender. The DNA, examined in this example, was provided by Professor Jorn Walter of the University of Saarland.

The DNA was bisulfite-converted as described in Example 1.

In both QM assays, bisulfite-specific primers (SEQ ID NO: 6, SEQ ID NO: 7) were used, which amplify a 161 bp long sequence of the IGF2 gene from mouse (SEQ ID NO: 12 bzw. SEQ ID NO: 13, NT_039437.4, nt909691-nt909851). The SD7-specific QM assay was calibrated with a mixture of SD7 DNA, and the BL6-specific QM assay was calibrated with a mixture of BL6 DNA. The entire methylated and unmethylated DNA was produced using SssI methyltransferase or through genome-wide amplification with phi29 polymerase (see Example 1). The results of the calibration of SD7-QM assays are depicted in FIG. 4, and those of the BL6-QM assays, in FIG. 5.

DNA from different tissues was obtained from mice of the crossbred BL6×SD7 as well as SD7×BL6 (first so-called strain is in each case female). 10 ng bisulfite-converted mouse DNA was measured in two trials with the BL6-specific QM assay and subsequently also with the SD7-specific QM assay. The examined CT values for the signal of methylated and unmethylated DNA are summarized in Table 3. The methylation rate for each respective allele was calculated (Table 4) from the CT values using the calibration (Tables 4 and 5). It was shown that for all the examined tissues only the chromosomes inherited from the father were methylated, whereas for the maternal chromosomes no methylation was evident. For the heart, intestines, and kidney tissues, the data for the reciprocal cross could be investigated, which in each case, showed good concordance: heart 21% and 24%, intestines 25% and 35%, kidney 13% and 23%. For brain and liver tissues, the only cross SD7×BL6 was available. The methylation rates, measured, yielded for the brain 3% and liver 55%. An overview of all the results is given as a chart in FIG. 6.

In the following, the reaction conditions are described in detail. The PCR reactions were performed in the LightCycler in 20 µl reaction volumes and contained:

10 µl of Template-DNA

2 µl PCR buffer (Qiagen, containing 1.5 mM MgCl2)

0.25 mg/ml BSA (Sigma, non acetylated)

0.25 mM dNTPs each (dATP, dTTP, dGTP, CTP, Fermentas)

3.0 mM $MgCl_2$ (Qiagen)

0.30 µM Forward primer (SEQ ID NO: 6, TIB-MolBiol)

0.30 µM Reverse primer (SEQ ID NO: 7, TIB-MolBiol)

0.15 µM Probe1 (SEQ ID NO: 8 or SEQ ID NO: 9, TIB-MolBiol)

0.15 µM Probe2 (SEQ ID NO: 10, TIB-MolBiol)

0.15 µM Probe3 (SEQ ID NO: 11, TIB-MolBiol)

2 Units HotStarTaq Polymerase (Qiagen)

The temperature-time-profile was programed as follows:

activation of polymerase: 15 min at 95° C.

50 temperature cycles: 10 sec at 95° C.

30 sec at 56° C.

10 sec at 72° C.

The analysis was performed with the SoFar software 1.1.1 (© 2005 Jochen Wilhelm). The detected CT values were analyzed according to the principle of the QM assay. The results are averages from 2 trials.

TABLE 3

Sequences

| SeqID | Name | Sequence |
|---|---|---|
| SEQ ID NO: 6 | IGF2-b2-F | TtAtTGATGGTTGtTGGAtATtTt |
| SEQ ID NO: 7 | IGF2-b2-R | aAaaCCTaCCTaCCCTCCTa |
| SEQ ID NO: 8 | IGF2-BL6-Fluo | TGGttTtTtTGAAtTtTTTGAGtTtT TTG-Fluo |
| SEQ ID NO: 9 | IGF2-SD7-Fluo | TGGttTtAtTGAAtGtTTTGAGtTtT TTG-Fluo |
| SEQ ID NO: 10 | IGF2_Red640 | red640-tAAGtATGCGAtttCGGCG G-Pho |
| SEQ ID NO: 11 | IGF2_Red705 | red705-tAAGtATGtGAttttGGtGGGtAt-Pho |
| SEQ ID NO: 12 | IGF2-amp-BL6 | TtAtTGATGGTTGtTGGAtATtTtCG AAGAGGtTttttCGTGGGCGGGGTtT TTGGGTGGTAAtACGATtAGGGGACG ATGACGTTTGGttTtTtTGAAtTtTT TGAGtTtTTTGGtAAGtATGCGAttt CGGCGGGtACGtAG-GAGGGtAGGtA GGttTt |
| SEQ ID NO: 13 | IGF2-amp-SD7 | TtAtTGATGGTTGtTGGAtATtTtCG AAGAGGtTttttCGTGGGCGGGGTtT TTGGGTGGTAAtACGATtAGGGGACG ATGACGTTTGGttTtAtTGAAtGtTT TGAGtTtTTTGGtAAGtATGCGAttt CGGCGGGtACGtAG-GAGGGtAGGtA GGttTt |

The abbreviations represent:
Fluo = Fluorescine,
red640 = LightCycler dye for 640 nm,
red705 = LightCycler dye for 705 nm,
Pho = 3'-Phosphate Modification.
Lower case letters indicated cytosine positions, which are converted through bisulfite-conversion into uracil or subsequently, into thymine in PCR. The underlined positions indicate two polymorphisms in the SD7 laboratory mouse strain at the positions nt909785 (T → A) as well as nt909792 (T → G).

TABLE 4

Results of the BL6-QM Assay.

| cross-breeding | tissue | % methylation (mean value) | | CT 640 nm (CG probe) | CT 705 nm (tG probe) | ratio | % methylation (single value) |
|---|---|---|---|---|---|---|---|
| BL6 × SD7 | Heart | 0 | 1. Measurement | >50 | 28.88 | 0 | 0 |
| | | | 2. Measurement | >50 | 29.02 | 0 | 0 |
| BL6 × SD7 | Intestine | 0 | 1. Measurement | >50 | 29.5 | 0 | 0 |
| | | | 2. Measurement | >50 | 29.4 | 0 | 0 |
| BL6 × SD7 | Kidney | 0 | 1. Measurement | >50 | 29.59 | 0 | 0 |
| | | | 2. Measurement | >50 | 28.91 | 0 | 0 |
| SD7 × BL6 | Brain | 0 | 1. Measurement | >50 | 28 | 0 | 0 |
| | | | 2. Measurement | >50 | 27.59 | 0 | 0 |
| SD7 × BL6 | Heart | 29 | 1. Measurement | 28.17 | 27.82 | 44 | 38 |
| | | | 2. Measurement | 28.5 | 27.538 | 32 | 20 |
| SD7 × BL6 | Intestine | 42 | 1. Measurement | 28.59 | 29.5 | 47 | 41 |
| | | | 2. Measurement | 28.77 | 28.66 | 48 | 44 |
| SD7 × BL6 | Kidney | 37 | 1. Measurement | 28.93 | 27.87 | 32 | 21 |
| | | | 2. Measurement | 27.88 | 28.11 | 54 | 52 |
| SD7 × BL6 | Liver | 47 | 1. Measurement | 27.71 | 28.36 | 61 | 62 |
| | | | 2. Measurement | 28.8 | 28.24 | 40 | 33 |

Measured CT for various tissues from different cross-strains as well as the outcome of the degree of methylation detected.

TABLE 5

Results of SD7-QM Assay.

| cross-breeding | tissue | % methylation (mean value) | | CT 640 nm (CG probe) | CT 705 nm (tG probe) | ratio | % methylation (single values) |
|---|---|---|---|---|---|---|---|
| BL6SD7 | Heart | 29 | 1. Measurement | >29.33 | 28.71 | 39 | 36 |
| | | | 2. Measurement | >29.83 | 28.62 | 30 | 22 |
| BL6SD7 | Intestine | 38 | 1. Measurement | >28.83 | 28.13 | 38 | 34 |
| | | | 2. Measurement | >28.42 | 28.04 | 43 | 42 |
| BL6SD7 | Kidney | 26 | 1. Measurement | >28.82 | 28 | 36 | 31 |
| | | | 2. Measurement | >29.19 | 27.91 | 29 | 21 |
| SD7BL6 | Brain | 0 | 1. Measurement | >50 | 28.57 | 0 | 0 |
| | | | 2. Measurement | >50 | 28.77 | 0 | 0 |
| SD7BL6 | Heart | 0 | 1. Measurement | >50 | 28.24 | 0 | 0 |
| | | | 2. Measurement | >50 | 28.47 | 0 | 0 |
| SD7BL6 | Intestine | 0 | 1. Measurement | >50 | 28.96 | 0 | 0 |
| | | | 2. Measurement | >50 | 29.37 | 0 | 0 |
| SD7BL6 | Kidney | 0 | 1. Measurement | >50 | 29.4 | 0 | 0 |
| | | | 2. Measurement | >50 | 29.86 | 0 | 0 |
| SD7BL6 | Liver | 0 | 1. Measurement | >50 | 29.17 | 0 | 0 |
| | | | 2. Measurement | >50 | 29.74 | 0 | 0 |

Measured CT values for various tissues from different crossbred as well as the methylation rates derived therefrom.

SEQUENCE LISTING

<160> NUMBER OF SEQ ID NOS: 13

Figure 1:
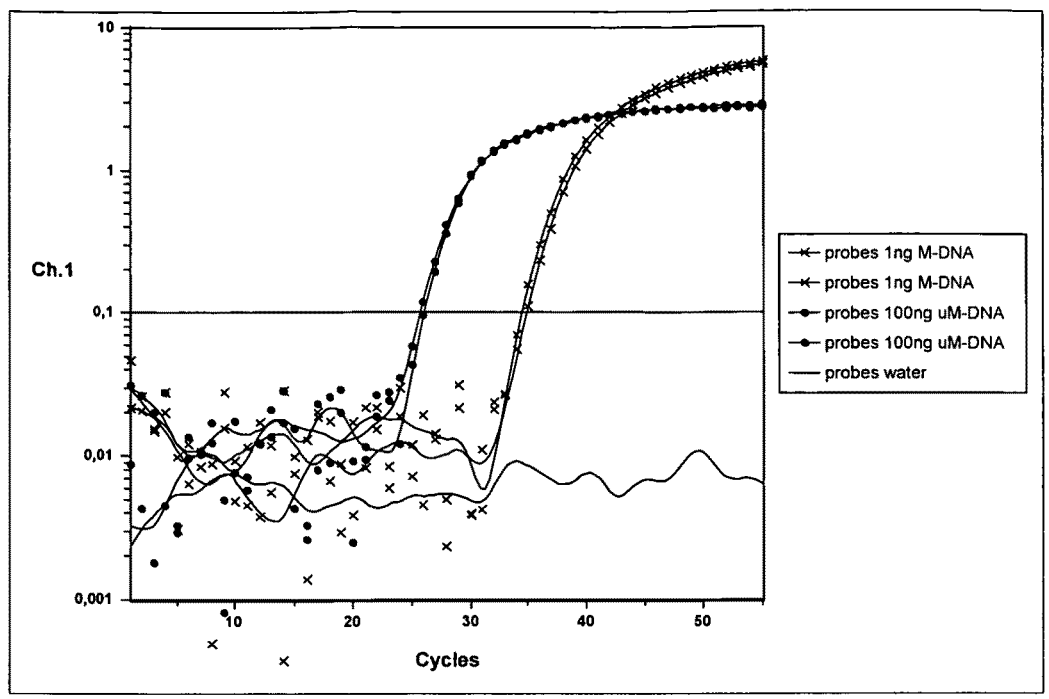
FIG. 1: Amplification curves of the described Real Time PCR in channel 530 nm. The detection of the entire DNA is performed independently of the methylation status through the use of a methylation-specific Taqman probe (SEQ ID NO: 3). 1 ng methylated DNA (cross-hatched lines; M-DNA) were measured with CT 36.0 and 36.5. The signals for the 100 ng unmethylated DNA (dotted lines; uM-DNA) were detected with CT 26.5 and 27.5.
Figure 2:
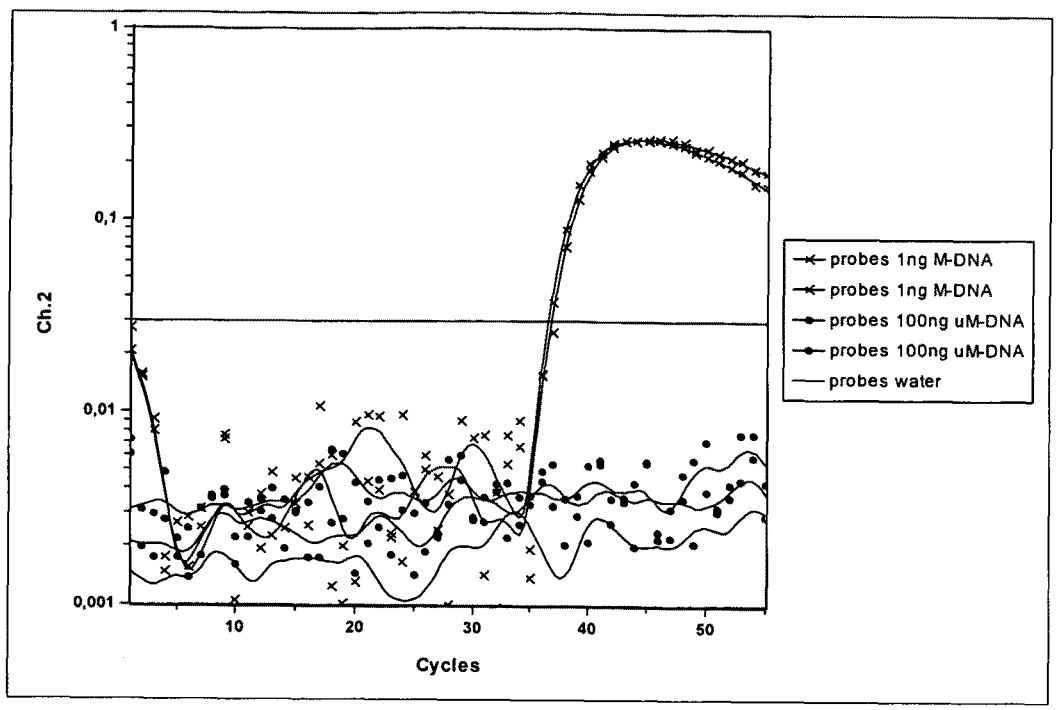
FIG. 2: Amplification curves of the described Real Time PCR in channel 640 nm. The methylation-specific LightCycler probe (SEQ ID NO: 4) serves to verify the methylated DNA. 1 ng methylated DNA (cross-hatched lines; M-DNA) were measured with a CT of 36.0 and 36.5. No signals were measured in the reactions with 100 ng unmethylated DNA (dotted lines; uM-DNA).
Figure 3:
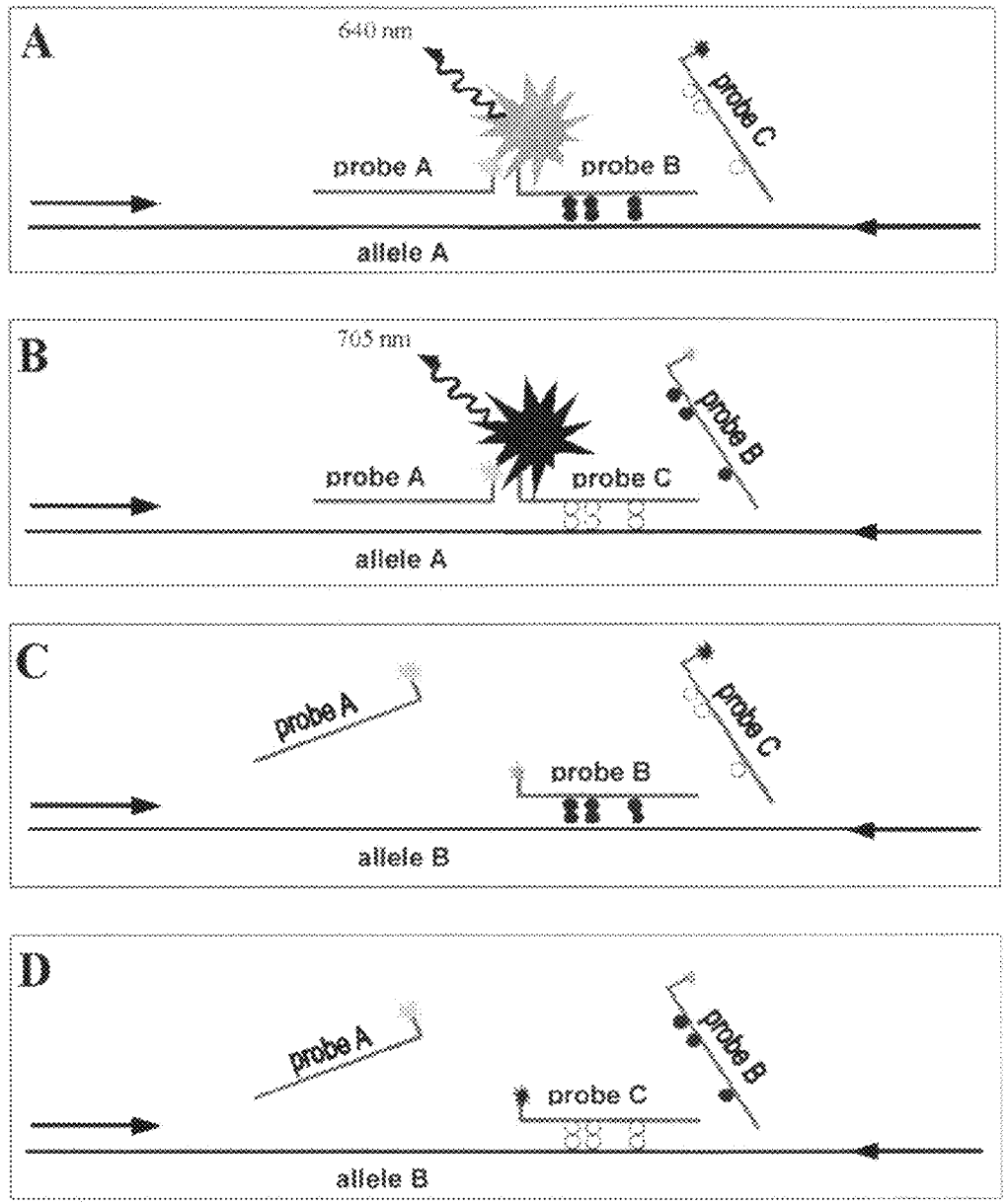
FIG. 3: Schematic depiction of allele-specific quantitative methylation assay (allele-specific QM assay). Probe A binds to the amplificate, when the allele A contains (Part A and B). Probe B binds adjacent to Probe A, when the sequence contains a methylated CpG position (Part A). Through the Fluorescence-Resonance-Energy-Transfer (FRET), a signal is excited at the wavelength 640 nm. If the original sequence is not methylated, probe C (Part B) binds and a signal is excited at 705 nm. If allele A is not included in the amplificate, then probe A will not bind and a signal is not excited (Part C and D).
Figure 4A:
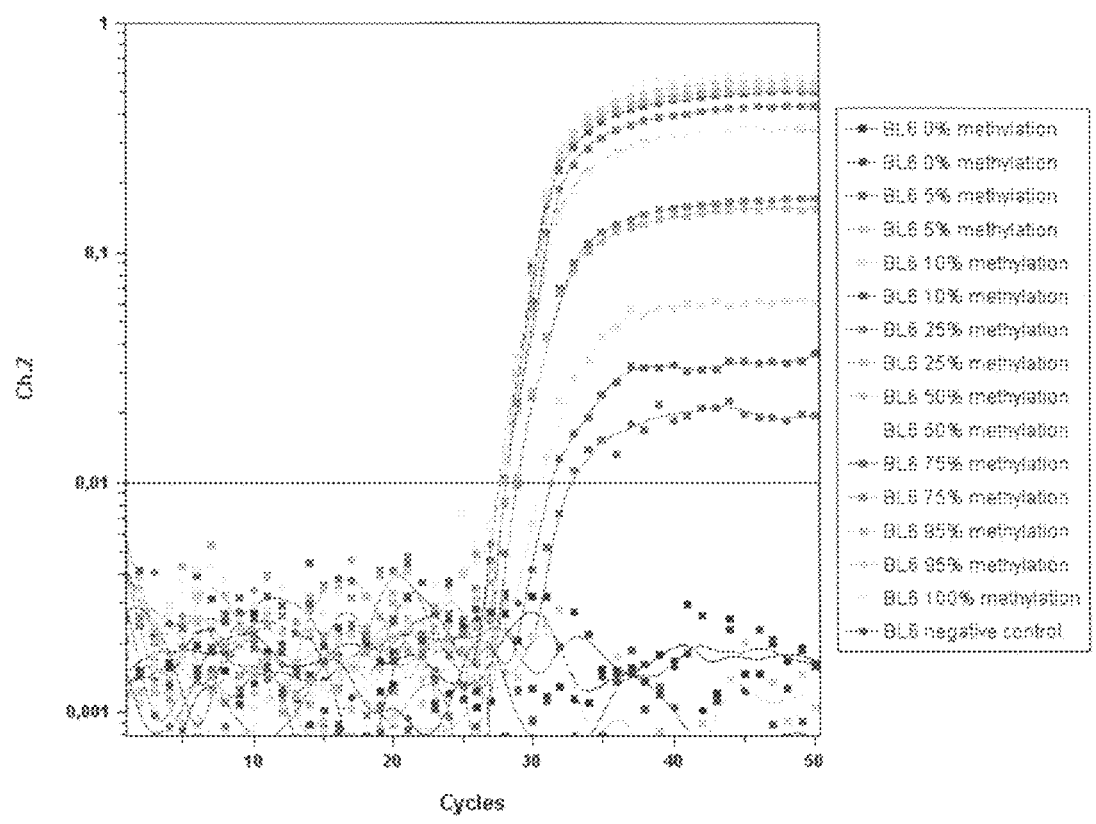
FIG. 4: Calibration of the BL6-specific QM assay. Methylated DNA is detected in channel Ch2 at 640 nm (FIG. 4a) and unmethylated DNA at channel Ch3 (705 nm) (FIG. 4b). 10 ng bisulfite-converted DNA was amplified from mixtures of 0, 5, 10, 25, 50, 75, 95 and 100% methylation. The difference of the CT values of the channels Ch2 and Ch3 was calculated for each data point and put into the formula Ratio=100/(1+2exp (deltaCT)). The ratio obtained is plotted against the percentage methylation of DNA mixture (FIG. 4c). The slope and axis intercept of the line of best fit were subsequently used for the calculation of methylation rates of tissue samples.
Figure 4B:
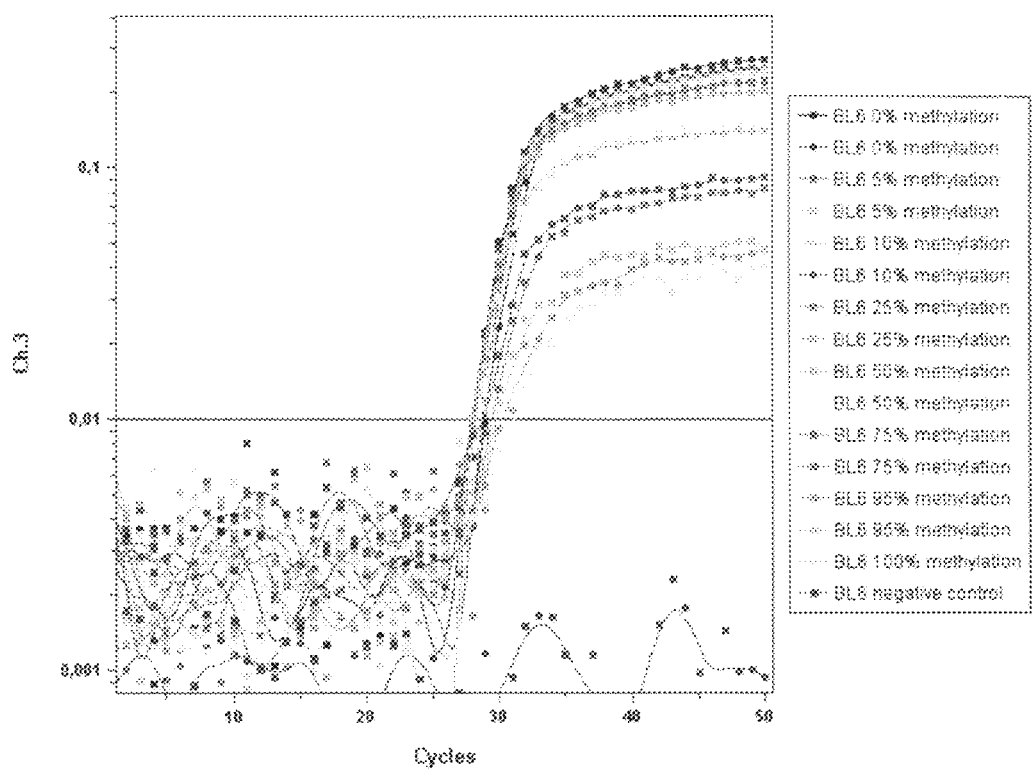
Figure 4C:
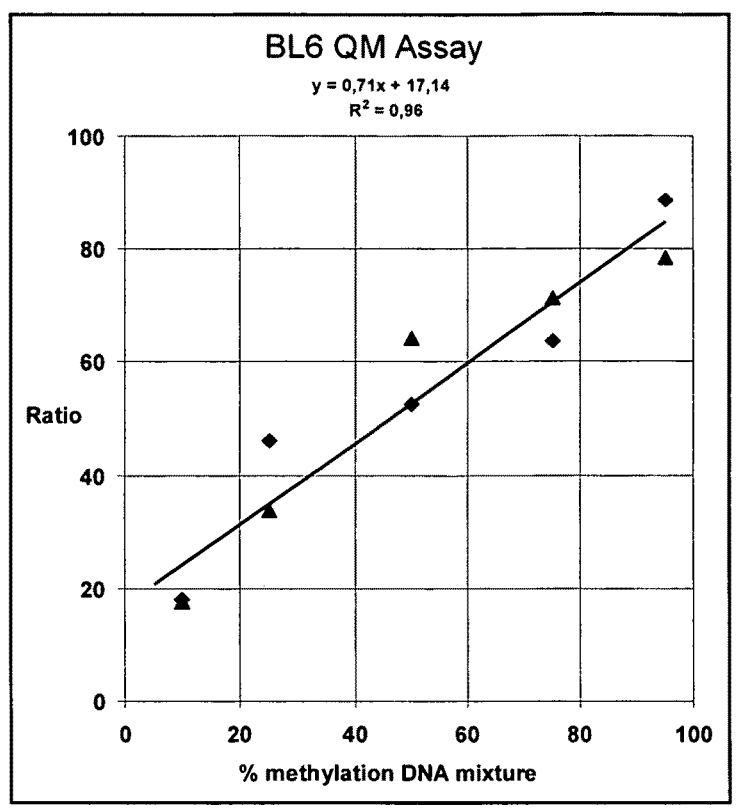
Figure 5A:
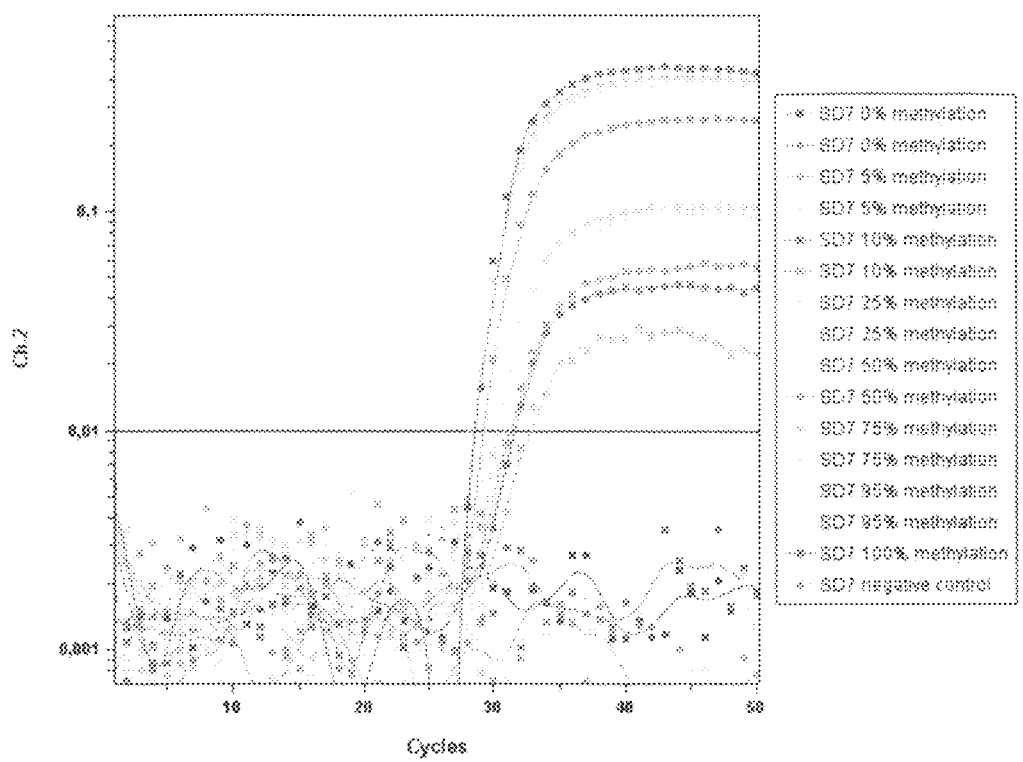
FIG. 5: Calibration of the SD7-specific QM assay. Calibration of the BL6-specific QM assay. Methylated DNA is detected in channel Ch2 at 640 nm (FIG. 5a), unmethylated DNA in channel Ch3 705 nm (FIG. 5b). 10 ng bisulfite-converted DNA was amplified from mixtures with 0, 5, 10, 25, 50, 75, 95 and 100% methylation. The difference of the CT values of the channels Ch2 and Ch3 was calculated for each data point and put into the formula Ratio=100/(1+2exp(deltaCT)). The ratio obtained is plotted against the percentage methylation of DNA mixture (FIG. 4c). The slope and axis intercept of the line of best fit were subsequently used for the calculation of the degree of methylation of tissue samples.
Figure 5B:
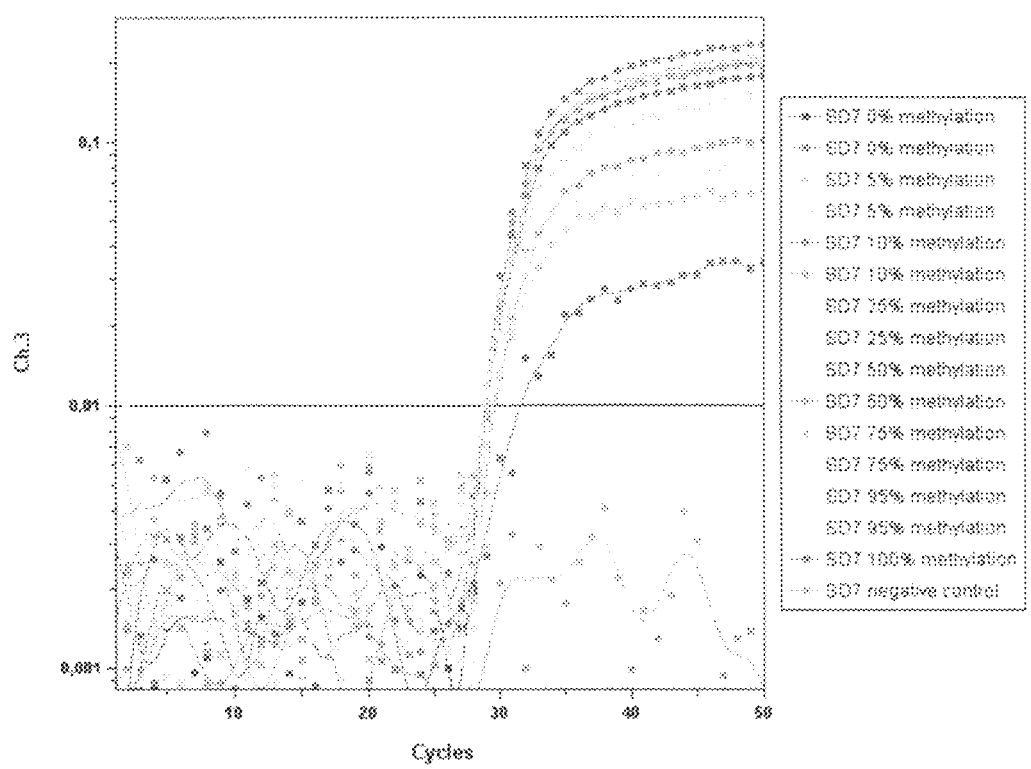
Figure 5C:
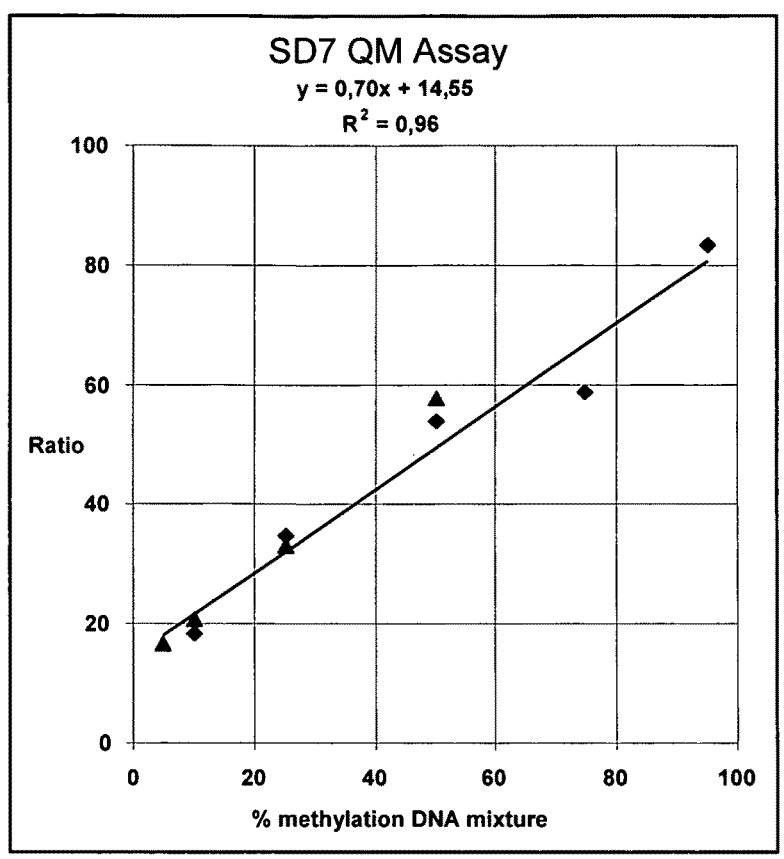
Figure 6:
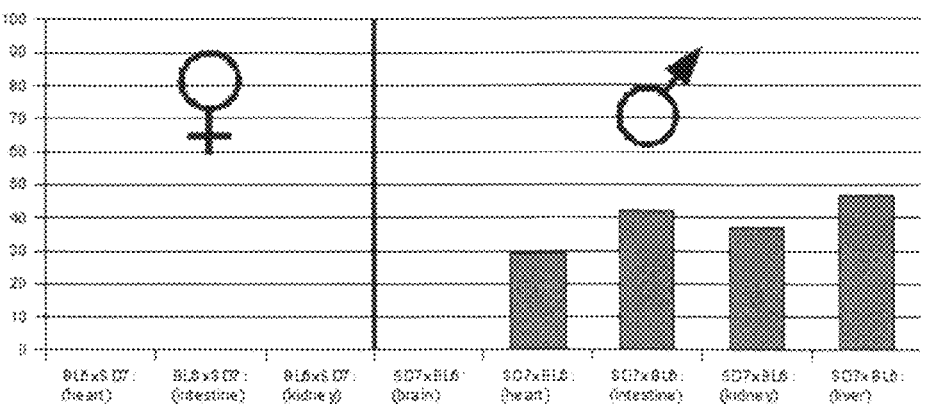
FIG. 6: Overview of allele-specific degree of methylation from various tissue samples. Part A of the figure shows the results of BL6-specific QM assay. In Part B, the results of SD7-specific QM assay are shown. The methylation of the maternally inherited chromosome was measured in both cross variations as 0%. For the paternally inherited chromosome, methylation rates between 0% and 47% were found, dependent on the type of tissue.
Figure 6:
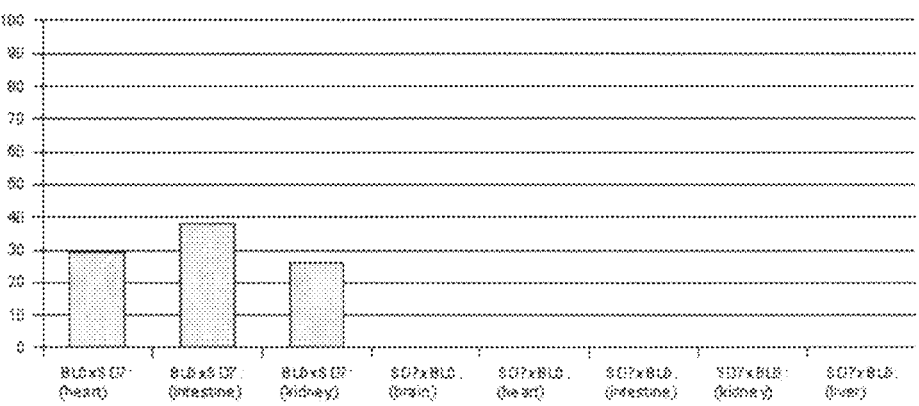

<210> SEQ ID NO 1
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 1
ttattgatgg ttgttggata tttt                                          24

<210> SEQ ID NO 2
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 2
aaaacctacc taccctccta                                               20

<210> SEQ ID NO 3
<211> LENGTH: 29
<212> TYPE: DNA
<213> ORGANISM: Artificial Sequence
<220> FEATURE:
<223> OTHER INFORMATION: chemically treated genomic DNA (Homo sapiens)

<400> SEQUENCE: 3
tggttttttt gaattttttg agttttttg                                     29

<210> SEQ ID NO 4
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 4
cgattagggg acgatgacg                                                19

<210> SEQ ID NO 5
<211> LENGTH: 161
<212> TYPE: DNA
<213> ORGANISM: Artificial Sequence
<220> FEATURE:
<223> OTHER INFORMATION: chemically treated genomic DNA (Homo sapiens)

<400> SEQUENCE: 5
ttattgatgg ttgttggata ttttcgaaga ggttttttcg tgggcggggt ttttgggtgg    60
taatacgatt aggggacgat gacgtttggt ttttttgaat ttttgagtt tttggtaag    120 tatgcgattt cggcgggtac gtaggagggt aggtaggttt t                       161

```
<210> SEQ ID NO 6
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 6
ttattgatgg ttgttggata tttt                                          24

<210> SEQ ID NO 7
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 7
aaaacctacc taccctccta                                               20

<210> SEQ ID NO 8
<211> LENGTH: 29
<212> TYPE: DNA
<213> ORGANISM: Artificial Sequence
<220> FEATURE:
<223> OTHER INFORMATION: chemically treated genomic DNA (Homo sapiens)

<400> SEQUENCE: 8 tggtttttt gaatttttg agttttttg                                       29

<210> SEQ ID NO 9
<211> LENGTH: 29
<212> TYPE: DNA
<213> ORGANISM: Artificial Sequence
<220> FEATURE:
<223> OTHER INFORMATION: chemically treated genomic DNA (Homo sapiens)

<400> SEQUENCE: 9 tggtttttatt gaatgttttg agttttttg                                    29

<210> SEQ ID NO 10
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 10
taagtatgcg atttcggcgg                                               20

<210> SEQ ID NO 11
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 11
taagtatgtg attttggtgg gtat                                          24

<210> SEQ ID NO 12
<211> LENGTH: 161
<212> TYPE: DNA
<213> ORGANISM: Artificial Sequence
<220> FEATURE:
<223> OTHER INFORMATION: chemically treated genomic DNA (Homo sapiens)
```

-continued

```
<400> SEQUENCE: 12
ttattgatgg ttgttggata ttttcgaaga ggtttttcg tgggcggggt ttttgggtgg      60
taatacgatt aggggacgat gacgtttggt tttttgaat ttttgagtt ttttggtaag     120 tatgcgattt cggcgggtac gtaggagggt aggtaggttt t                       161

<210> SEQ ID NO 13
<211> LENGTH: 161
<212> TYPE: DNA
<213> ORGANISM: Artificial Sequence
<220> FEATURE:
<223> OTHER INFORMATION: chemically treated genomic DNA (Homo sapiens)

<400> SEQUENCE: 13
ttattgatgg ttgttggata ttttcgaaga ggtttttcg tgggcggggt ttttgggtgg      60
taatacgatt aggggacgat gacgtttggt tttattgaat gttttgagtt ttttggtaag    120
tatgcgattt cggcgggtac gtaggagggt aggtaggttt t                       161
```

The invention claimed is:

1. A method for quantifying the degree of methylation of a target DNA sequence, comprising:
   a) converting unmethylated cytosine in a target DNA sequence to uracil or to another base that can be distinguished from cytosine based on its base-pairing behavior, wherein 5-methylcytosine remains unconverted;
   b) amplifying the converted target DNA sequence in the presence of two real-time probes, which bind to the same amplificate in the same vessel, wherein:
      (i) a first probe is specific for the methylated state or the unmethylated state of the target DNA sequence,
      (ii) a second probe does not carry a CpG dinucleotide and no TG- or CA-dinucleotide whose cytosine base was converted by the treatment of step a),
      (iii) each probe contains a pair of labels that permits the independent detection of each probe, and
      (iv) each of the two probes hybridize to the converted target DNA sequence;
   c) detecting each pair of labels independent of the other pair;
   d) determining the extent to which the amplification has proceeded by detecting the hybridized probe signals at various time points, wherein the signal generated by the first probe is generated independently of the signal of the second probe; and
   e) determining the degree of methylation of the target DNA sequence by determining the ratio of signal intensities for the first and second probes.

2. The method of claim 1, wherein the degree of methylation is determined from the ratio of the signal intensities at a certain time during the exponential phase of amplification.

3. The method of claim 2, wherein the degree of methylation is determined from the ratio of the signal intensities at a time point that lies 5 cycles before or after the time point at which the amplification reaches its maximal slope (point of inflection of the fluorescence intensity curves).

4. The method of claim 3, wherein the degree of methylation is determined from the ratio of the signal intensities at a time point that lies 2 cycles before or after the time point at which the amplification reaches its maximal slope.

5. The method of claim 4, wherein the degree of methylation is determined from the ratio of the signal intensities at a time point that lies 1 cycle before or after the time point at which the amplification reaches its maximal slope.

6. The method of claim 5, wherein the degree of methylation is determined from the ratio of the signal intensities at a time point at which the amplification reaches its maximal slope (point of inflection of the fluorescence intensity curves).

7. The method of claim 1, wherein the calculation of the degree of methylation is performed via the ratio of threshold values at which a certain signal intensity is exceeded.

8. The method of claim 7, wherein the calculation is performed via a ratio of Ct values.

9. The method of claim 8, wherein the calculation is performed via a formula according to: degree of methylation $100/(1+2^{\Delta Ct})$.

10. The method of claim 1, wherein the ratio is area under, or maximal slope of, two fluorescence intensity curves at different wavelengths.

11. The method of claim 10, wherein the fluorescence intensity curves show the time point of the exponential amplification a minimal interception with the y-axis and a maximal Fischer score.

12. The method of claim 10, wherein the fluorescence intensity curves have the time point of the exponential amplification a slope and a regression value near 1.

13. The method of claim 1, wherein the result is compared to a standard curve.

14. The method of claim 1, wherein the first and second probes interact with each other through FRET.

15. The method of claim 1, wherein the second probe is a Taqman probe, wherein a fluorescent dye is localized to the 3' end of the Taqman probe and a quencher molecule is attached to the Taqman probe at a location 5' of the fluorescent dye.

16. The method of claim 1, wherein the first probe is a Lightcycler probe whose fluorescent dye is excited by the fluorescent dye of the Taqman probe.

17. The method of claim 1, further comprising providing a diagnosis of cancer or of another disease associated with a change in methylation.

18. The method of claim 1, further comprising providing a prediction of adverse effects of pharmaceuticals, a distinction between cell types or tissues, or an examination of cell differentiation.

19. A method for quantifying the degree of methylation of a target DNA sequence, comprising:
   a) converting unmethylated cytosine in a target DNA sequence to uracil or to another base that can be distinguished from cytosine based on its base-pairing behavior, wherein 5-methylcytosine remains unconverted;
   b) amplifying the converted target DNA sequence in the presence of two real-time probes, which bind to the same amplificate in the same vessel, wherein:
   (i) a first probe is specific for the methylated state or the unmethylated state of the target DNA sequence,
   (ii) a second probe does not carry a CpG dinucleotide and no TG- or CA-dinucleotide whose cytosine base was converted by the treatment of step a),
   (iii) one probe contains a pair of labels and the other probe contains a single dye thereby permitting independent detection of each probe, and
   (iv) each of the two probes hybridize to the converted target DNA sequence;
   c) detecting a first signal generated from the first probe and a distinct second signal generated from the second probe;
   d) determining the extent to which the amplification has proceeded by detecting the hybridized probe signals at various time points, wherein the signal generated by the first probe is generated independently of the signal of the second probe; and
   e) determining the degree of methylation of the target DNA sequence by determining the ratio of signal intensities for the first and second probes.

20. The method of claim 19, wherein the second probe of (ii) is a Taqman probe, wherein a fluorescent dye is localized to the 3' end of the Taqman probe and a quencher molecule is attached to the Taqman probe at a location 5' of the fluorescent dye.

21. The method of claim 20, wherein the first probe of (i) is a Lightcycler probe whose fluorescent dye is excited by the fluorescent dye of the Taqman probe.

* * * * *